United States Patent [19]
Surmatis

[11] 3,966,734
[45] June 29, 1976

[54] METHOD FOR THE PURIFICATION OF 6-METHOXY-1-PHENAZINOL 5,10-DIOXIDE

[75] Inventor: Joseph Donald Surmatis, West Caldwell, N.J.

[73] Assignee: Hoffmann-La Roche Inc., Nutley, N.J.

[22] Filed: Feb. 12, 1975

[21] Appl. No.: 549,413

Related U.S. Application Data

[60] Division of Ser. No. 213,748, Dec. 29, 1971, abandoned, which is a continuation-in-part of Ser. No. 139,287, April 23, 1971, abandoned.

[52] U.S. Cl. .............................. 260/267; 260/242; 424/245
[51] Int. Cl.² .................................. C07D 241/52
[58] Field of Search ....................... 260/267, 242

[56] References Cited
UNITED STATES PATENTS
3,586,674   6/1971   Leimgruber et al. ............... 260/242

Primary Examiner—Paul M. Coughlan, Jr.
Attorney, Agent, or Firm—Samuel L. Welt; Bernard S. Leon; William M. Farley

[57] ABSTRACT

A novel improved procedure is described for the preparation of various metal complexes of 6-methoxy-1-phenazinol 5,10-dioxide by the reaction between 6-methoxy-1-phenazinol 5,10-dioxide and a metal salt or hydroxide in an aqueous suspension or a solution in aqueous mineral acid. Preferred metals disclosed as suitable for use in the process are calcium, strontium, magnesium and iron. Utility of the ferric chloride complex and the calcium complex in the purification of 6-methoxy-1-phenazinol 5,10-dioxide is also disclosed.

3 Claims, No Drawings

METHOD FOR THE PURIFICATION OF 6-METHOXY-1-PHENAZINOL 5,10-DIOXIDE

RELATED APPLICATION

This application is a division of application Ser. No. 213,748, filed Dec. 29, 1971, and now abandoned, which was, in turn, a continuation-in-part of application Ser. No. 139,287, filed Apr. 23, 1971 and now abandoned.

BACKGROUND OF THE INVENTION

Metal complexes of 6-methoxy-1-phenazinol 5,10-dioxide (referred to hereinafter as myxin) heretofore were prepared by combining a saturated solution of myxin in a suitable organic solvent with a saturated solution of a metal salt in the same solvent. The precursor, myxin, is readily prepared by selective alkylation of iodinin (1,6-phenazindiol 5,10-dioxide).

Exemplary of the organic solvents generally employed in the prior processes used to prepare the metal complexes are acetic acid, acetonitrile, methanol, ether, chloroform, etc.

Preferably a solvent or solvent mixture in which both the myxin and the metal salts are more soluble than the metal complex formed by their reaction is used in these processes since the complex is isolated by precipitation from said solvents. This reaction may be carried out at room temperature or, to facilitate solution of the reactants and reduce the amount of solvent needed, at temperatures above room temperature.

The metal complexes of myxin have a high degree and wide spectrum of anti-microbial activity both in in vitro tests and in in vivo topical infections. In particular, the metal complexes have demonstrated a high level of activity against a wide variety of both gram positive and gram negative bacteria, fungi, protozoa and helminths. This wide spectrum of anti-microbial activity has manifested itself by the efficacy of the metal complexes as chemotherapeutic agents in combating topical infections.

There are, however, several drawbacks and deficiencies in the use of organic materials as solvents in the preparation of the metal complexes. One evident drawback is, of course, the relatively large volume of solvent which must be used. In addition, the preferred solvent, acetonitrile, is flammable and its use in conjunction with the metal complexes is hazardous. Myxin itself is highly flammable and sensitive to electrostatic discharge. Further, the metal complexes, on standing, have a tendency to form aggregates of from about 400 to about 600 microns in size after isolation and purification from these organic solvent systems. Finally, many metal complexes either cannot be prepared using organic solvents in such procedures or, if prepared, cannot be isolated therefrom by crystallization.

In the use of myxin's anti-microbial activity, a high purity material is, of course, advantageous. However, purification of myxin is expensive, difficult, time consuming and requires elaborate equipment, i.e., column chromatography.

There is thus a need for a method which overcomes these drawbacks and deficiencies. This inventin provides a method for the preparation and isolation of metal complexes of myxin which eliminates the problems inherent in the use of organic solvents, and provides a non-agglomerating product in crystalline form.

In another aspect, this invention provides methods for utilizing both the ferric chloride complex and the calcium complex of myxin to purify myxin.

BRIEF DESCRIPTION OF THE INVENTION

This invention relates to a novel method for the preparation of metal complexes of myxin using water or an aqueous mineral acid as the reaction medium. The invention also relates to the metal complexes per se, to compositions containing these metal complexes and to the use of these complexes both as chemotherapeutic agents in combating various microbial infections and, in the case of the ferric chloride complex and the calcium complex, as a means of purifying myxin.

DETAILED DESCRIPTION OF THE INVENTION

More specifically, this invention relates to a novel process for the preparation of metal complexes of myxin by the reaction in water or aqueous mineral acids of myxin and the corresponding salt or hydroxide of a pharmaceutically acceptable metal. The phrase "pharmaceutically acceptable metal" as used herein denotes those metals which are non-poisonous when utilized as part of a compound in a pharmaceutical composition. Typical of such metals are zinc, iron, magnesium, calcium, aluminum, strontium and the like. The preferred metal complexes of this invention are those formed from calcium, magnesium, strontium and iron.

The novel process of this invention involves the reaction in water or aqueous mineal acids of myxin with a salt or hydroxide of the desired metal. The metal complexes can be isolated as crystals by precipitation from the reaction medium. The complex formed by the process of this invention can readily be prepared by simply combining an aqueous suspension or a solution in aqueous mineral acid, at a temperature of from about 20°C. to about 100°C., of myxin and a salt or a hydroxide of a pharmaceutically acceptable metal. Where calcium and magnesium salts or hydroxides are used in an aqueous suspension, the reaction takes place in a solid state suspension since both reactants are either insoluble in water or very slightly soluble therein. The insoluble complex which forms is separated by filtration or precipitation.

Since myxin is very slightly soluble in water, myxin crystals are added to water and suspended therein by agitation. Some myxin goes into solution as evidenced by the light pink tinge which appears in the water. While the concentration of myxin is not a critical factor per se, its limiting factor is the resultant increase in viscosity to an unsatisfactorily high level at a concentration of 100 grams per liter or higher. The preferred concentration range is from 8–20 grams of myxin per liter of water.

Salts or hydroxides of the aforesaid metals can be used in this process.

The mole ratio of myxin to the metal salt or hydroxide should be about equimolar with, preferably, a slight excess of the metal salt or hydroxide, e.g., 0.75 moles of myxin per 1.25 moles of the metal salt, to insure reaction of all the myxin present in the aqueous suspension.

The reaction temperature and the reaction time are also not critical factors. The temperature can range from room temperature (20°–25°C.) up to 90°–95°C. and is selected based on other desiderata such as salt solubility and reaction time. Completeness of reaction is noted by the appearance of a greenblack suspension (metal complex of myxin) and the complete absence of any red specks of myxin therein.

Myxin has a high degree and wide spectrum of antimicrobial activity in both in vitro tests and in vivo topical infections. The metal complexes of myxin also exhibit this high degree and wide spectrum of antimicrobial activity.

For example, the anti-microbial activity of calcium myxin dihydrate, prepared by the method of this invention, is evaluated and compared to that of myxin itself both in vivo against 4 strains of bacteria and in vitro against yeast and fungus infections. The table below shows this anti-microbial efficacy.

Anti-microbial Activity of Myxin and Calcium Myxin Dihydrate Prepared in Water

| Organism | In Vivo $ED_{50}$, mcg/ml | |
|---|---|---|
| | Calcium Myxin Dihydrate | Myxin |
| S. agalactiae | <4 | 1 |
| S. aureus | <20 | 13 |
| E. coli | 60 | 8 |
| P. aeruginosa | 20 | 30 |

| | In Vitro Minimum Inhibitory Concentration, mcg/ml. | | | |
|---|---|---|---|---|
| | Calcium Myxin Dihydrate | | Myxin | |
| Organism | static | cidal | static | cidal |
| C. albicans | <0.8 | <0.8 | 1.8 | 23 |
| M. canis | <0.8 | <0.8 | 0.9 | 0.9 |

When compounds of this invention are employed in the treatment of microbial infection they are conveniently utilized in compositions with suitable carrier materials for use as chemotherapeutic agents in combating mammalian disease. They are formulated by uniformly distributing in a vehicle that is chemically compatible with the particular compound, non-inhibiting with respect to the active ingredient and essentially non-injurious to body tissue under the conditions of use. When formulated into compositions suitable for topical administration, the novel compounds of this invention are preferably employed in amounts ranging from about 0.1% to about 1.5% by weight of the chemotherapeutic composition, e.g., gel, cream, ointment, suspension, suppository or the like. It will be understood that the compounds of this invention, when employed in forms suitable for topical administration may be utilized in diverse formulations: for example, solid formulations including finely divided powders and granular materials, liquid formulations including suspensions, concentrations, slurries, tinctures, aerosols and the like, depending on the application intended and the formulation media desired. They may be employed as creams, gels, jellies, ointments, pastes, etc. Formulations containing ingredients which have reactivity with the complexes of this invention may alter the mole ratios of the components of the complex since such ingredients can be incorporated into the complex as ligands. This invention is intended to include such compositions.

In the preparation of myxin, the crude product is contaminated with, for example, solvent, unreacted iodinin starting material and such by-products and degradation products as 6-methoxy-1-phenazinol-10-oxide; 1,6-dimethoxyphenazine 10-oxide and 1,6-dimethoxyphenazine 5,10-dioxide. Heretofore purification of this crude product was achieved by such tedious and timeconsuming procedures as column chromatography.

Using the ferric chloride complex prepared by the process of this invention, however, it has been found that myxin purification can be achieved in a simple process involving the preparation and isolation of the ferric chloride complex from crude myxin followed by the breaking of the complex with acetone to yield a pure myxin. This myxin purification is specific to the ferric complex made by the process of this invention since processes for complex formation using organic solvents require a pure myxin as the starting material.

In addition, in the purification of myxin by the above ferric complex method, a crude myxin residue wherein the main impurity is 1,6-dimethoxyphenazine 5,10-dioxide (dimethoxy iodinin) remains. Formation, by the process of this invention, of the calcium complex of myxin from this crude myxin residue wherein the dimethoxyiodinin remains unchanged, isolation of the complex from the dimethoxyiodinin and subsequent breaking of the calcium complex yields pure myxin.

The following examples illustrate the invention.

EXAMPLE 1

Preparation of 6-methoxy-1-phenazinol 5,10-dioxide, calcium dihydrate complex

To 10 liters of distilled water heated to 50°C. are added, with stirring, 16 grams of calcium hydroxide. After 10 minutes, 51.5 grams of myxin are added with vigorous stirring. The reaction mixture is heated to 80°C. and maintained at that temperature under agitation for 2 hours. The mixture is then cooled to room temperature. The black solid which precipitates is filtered, washed with distilled water (2 × 1,000 ml.) and acetone (3 × 1,000 ml.) dried at 55°–60°C. and 0.1 mm for 20 hours. The resulting calcium myxin dihydrate is a crystalline powder having the following characteristics:

Calculated for $C_{26}H_{22}N_4O_{10}Ca$: C, 52.88; H, 3.75; Ca, 6.77

Found: C, 53.07; H, 3.58; Ca, 6.83

Visible ultraviolet absorption maxima (in 0.1N methanolic HCl):

| 512 nm a | 25.2 |
| 355 nm a | 16.7 |
| 286 nm a | 308.7 |

EXAMPLE 2

Preparation of 6-methoxy-1-phenazinol 5,10-dioxide, strontium dihydrate complex

To 500 milliliters of distilled water are added, with stirring, 9 grams of strontium hydroxide octahydrate. After 10 minutes, 9 grams of myxin are added with vigorous stirring. The reaction mixture is heated to 80°C. and maintained at that temperature under agitation for 2 hours. The mixture is then cooled to room temperature and the finely divided solid, i.e., strontium myxin, is filtered, washed with distilled water (3 × 500 ml.), acetone (2 × 500 ml.), methylene chloride (2 × 500 ml.) and acetone (1 × 500 ml.). The product is dried at 60°C. and 0.1 mm for 20 hours. The resulting strontium myxin dihydrate is characterized as follows:

Calculated for: $C_{26}H_{22}N_4O_{10}Sr$: Sr, 13.73;

Found: Sr, 14.22

EXAMPLE 3

Preparation of 6-methoxy-1-phenazinol 5,10-dioxide, ferric chloride complex

To 250 ml. of aqueous hydrochloric acid (37%), 10 grams of myxin are added, with stirring. After 10 minutes, 10 grams of ferric chloride hexahydrate are added with agitation continued for 16 hours. The resulting black solid is filtered, washed with hydrochloric acid (1 × 100 ml.), acetic acid (1 × 100 ml.), and methylene chloride (2 × 500 ml.). The product is then dried at 60°C. and 0.1 mm for 20 hours. The resulting ferric chloride myxin complex is characterized as follows:

Calculated for: $C_{13}H_{10}N_2O_4 \cdot HCl \cdot FeCl_3$: Fe, 12.22; C, 34.17; H, 2.43; N, 6.13

Found: Fe, 12.22; C, 34.39; H, 2.52; N, 6.26.

EXAMPLE 4

Preparation of 6-methoxy-1-phenazinol 5,10-dioxide, magnesium dihydrate complex

To 10 liters of distilled water preheated to 50°C., 12.8 grams of magnesium hydroxide is added with stirring. After 10 minutes, 51.5 grams of myxin is added with vigorous stirring. The reaction mixture is then heated to 80°C. and maintained at that temperature under agitation for 2 hours. The mixture is then cooled to room temperature. The resulting black solid precipitate is filtered, washed with distilled water (2 × 1,000 ml.) and acetone (3 × 1,000 ml.) and dried at 55°-60°C. and 0.1 mm for 20 hours. The product, magnesium myxin dihydrate, is characterized as follows:

Melting point 142° (with decomposition)

Calculated for: $C_{26}H_{22}N_4O_{10}Mg$: C, 65.36; H, 3.83; Mg, 4.18

Found: Mg, 4.22.

EXAMPLE 5

5.6 kg. of a 30% solids paste, from a preparatory procedure for myxin and containing 60% myxin, are charged to a reaction kettle containing 29 liters of concentrated hydrochloric acid, stirred for 30 minutes during which a blue color believed to result from a protonated myxin complex in the acid develops and then filtered to remove undissolved impurities using a two-inch layer of Hyflo (an inert silica). The filter cake is washed with 3 liters of concentrated hydrochloric acid to remove any uncomplexed myxin thereon and the acid solution is returned to the reaction kettle. One kilogram of ferric chloride hexahydrate is added to the kettle with stirring for one hour. The black solid ferric chloride complex of myxin which forms is vacuum filtered and washed with 4 liters of acetic acid and then with 8 liters of chloroform.

The ferric chloride complex is returned to a reaction kettle containing 20 liters of acetone at 10°C. and stirred overnight at that temperature. The resulting crystallized myxin is separated by filtration, washed until neutral with water followed by an acetone wash, and dried under vacuum at 60°C.

The acetone filtrates are combined, diluted with water, extracted with methylene chloride and concentrated under vacuum to yield additional myxin as a crude product containing approximately 70% of myxin and such impurities as 6-methoxy-1-phenazinol and, mainly, dimethoxyiodinin, 1,6-dimethoxyphenazine 5,10-dioxide.

EXAMPLE 6

2.0 kg. of crude dry myxin, from a preparatory procedure for myxin and containing 65% myxin, is added with stirring to a reaction kettle containing 60 liters of 50% aqueous sulfuric acid at 25°C. Stirring is continued for 30 minutes and then the solution is filtered through a 2-inch layer of Hyflo to remove undissolved impurities. The filter cake is washed with 4 liters of 50% sulfuric acid to remove any uncomplexed myxin thereon while retaining unreacted iodinin.

The blue-colored filtrate is returned to the reaction kettle. Two kg. of ferric chloride hexahydrate is added to the kettle with stirring for 1 hour. The resulting black solid is vacuum filtered and washed with 8 liters of acetic acid followed by 16 liters of chloroform.

The black ferric complex is returned to the kettle containing 30 liters of acetone and stirred for 20 hours at 10°C. The resulting crystallized myxin is separated by filtration, washed with water and with acetone and dried under vacuum at 60°C.

The acetone solutions are combined, diluted with water, extracted with methylene chloride, and concentrated under vacuum to yield additional myxin as a crude product wherein the main impurity is dimethoxyiodinin.

EXAMPLE 7

This example illustrates the use of the calcium complex of myxin, prepared by the process of this invention, in the purification of the crude myxin product, rich in dimethoxyiodinin, obtained from the purification processes described in Examples 5 and 6 above.

To a 12-liter flask containing 10 liters of water and 200 g. of calcium hydroxide are added 200 g. of the second crude myxin product, containing 20-25% of dimethoxyiodinin, obtained as the residue of the process of Example 6. The mixture is stirred for 2 hours at 80°C., cooled to room temperature and vacuum filtered. The solid is washed with cold (20°-25°C.) acetone and then stirred with two liters of boiling acetone. This washing procedure is repeated until, as determined by Triple Layer Chromatography, all of the soluble orange-colored dimethoxyiodinin is washed from the solid black calcium complex of myxin.

The calcium complex is added to 6 liters of 10% hydrochloric acid and stirred for 1 hour. Pure myxin, which separates as a red solid, is separated by filtration, washed with water until neutral and then with acetone, and dried under vacuum.

I claim:

1. A process for preparing pure 6-methoxy-1-phenazinol 5,10-dioxide which comprises
   a. reacting a ferric chloride hexahydrate in a suspension of a crude mixture containing 6-methoxy-1-phenazinol 5,10-dioxide in a concentrated aqueous mineral acid;
   b. isolating the solid ferric chloride complex of 6-methoxy-1-phenazinol 5,10-dioxide which forms;
   C admixing this complex with acetone, thereby breaking the complex; c.
   d. recovering the pure 6-methoxy-1-phenazinol 5,10-dioxide, wherein the concentrated aqueous mineral acid is selected from the group consisting of hydrochloric acid and sulfuric acid.

2. A process as described in claim 1 wherein the acid is hydrochloric acid.

3. A process as described in claim 1 wherein the acid is sulfuric acid.

* * * * *